United States Patent
Payne, Jr.

(10) Patent No.: US 7,158,822 B2
(45) Date of Patent: Jan. 2, 2007

(54) ELECTRODE HOLDER, HEADWEAR, AND WIRE JACKET ADAPTED FOR USE IN SLEEP APNEA TESTING

(75) Inventor: Charles E. Payne, Jr., Charlotte, NC (US)

(73) Assignee: Headwear, LLC, Charlotte, NC (US)

( * ) Notice: Subject to any disclaimer, the term of this patent is extended or adjusted under 35 U.S.C. 154(b) by 303 days.

(21) Appl. No.: 10/868,651

(22) Filed: Jun. 15, 2004

(65) Prior Publication Data

US 2005/0277821 A1    Dec. 15, 2005

(51) Int. Cl.
*A61B 5/04*    (2006.01)

(52) U.S. Cl. .................. 600/390; 607/149; 24/306
(58) Field of Classification Search ........... 600/390
See application file for complete search history.

(56) References Cited

U.S. PATENT DOCUMENTS

| | | | |
|---|---|---|---|
| 1,752,418 A * | 4/1930 | Clark et al. ............... 24/95 |
| 2,549,836 A * | 4/1951 | McIntyre et al. .......... 600/383 |
| 2,685,881 A * | 8/1954 | Kelly ...................... 600/382 |
| 2,895,479 A * | 7/1959 | Lloyd ...................... 600/384 |
| 4,033,333 A * | 7/1977 | DeSalvo et al. .......... 600/393 |
| 4,665,566 A | 5/1987 | Garrow |
| 4,836,200 A | 6/1989 | Clark |
| 4,996,989 A * | 3/1991 | Stundel et al. ........... 600/383 |
| 5,188,101 A | 2/1993 | Tumolo |
| 5,217,294 A | 6/1993 | Liston |
| 5,282,616 A * | 2/1994 | Stacavich-Notaro ....... 24/306 |
| 5,682,881 A | 11/1997 | Winthrop et al. |
| 5,687,715 A | 11/1997 | Landis et al. |
| 5,724,965 A | 3/1998 | Handke et al. |
| 5,893,365 A | 4/1999 | Anderson |
| 6,019,101 A | 2/2000 | Cotner et al. |
| 6,044,844 A | 4/2000 | Kwok et al. |
| 6,105,575 A | 8/2000 | Estes et al. |
| 6,171,258 B1 | 1/2001 | Karakasoglu et al. |
| 6,192,886 B1 | 2/2001 | Rudolph |

OTHER PUBLICATIONS

InnoMed Technologies; Defeating the World-Wide Sleep Apnea Crisis . . . ; www.nasal-aire.com; pp. 1-10; Published Prior to Jun. 26, 2002.

CPAP-Direct.com & HME-Direct.com. A Division of Breathing Disorders Services, Inc.; Internet Search for CPAP Headgear; www.cpap-direct.com; pp. 1-4; Published Prior to Jun. 26, 2002.

* cited by examiner

*Primary Examiner*—Lee S. Cohen
(74) *Attorney, Agent, or Firm*—Schwartz Law Firm P.C.

(57) ABSTRACT

An electrode holder is adapted for cooperating with a strap applied to a body part of a patient to hold a surface electrode to the skin. The electrode holder includes a base and a post projecting from the base. The post is adapted for extending through the strap and into a cavity formed with the electrode. The electrode holder is releasably attached to the strap by mating hook and loop fasteners. Once attached, the post of the holder secures the electrode in position thereby reducing motion artifacts caused by disturbance of the electrode after placement against the skin of the patient.

16 Claims, 19 Drawing Sheets

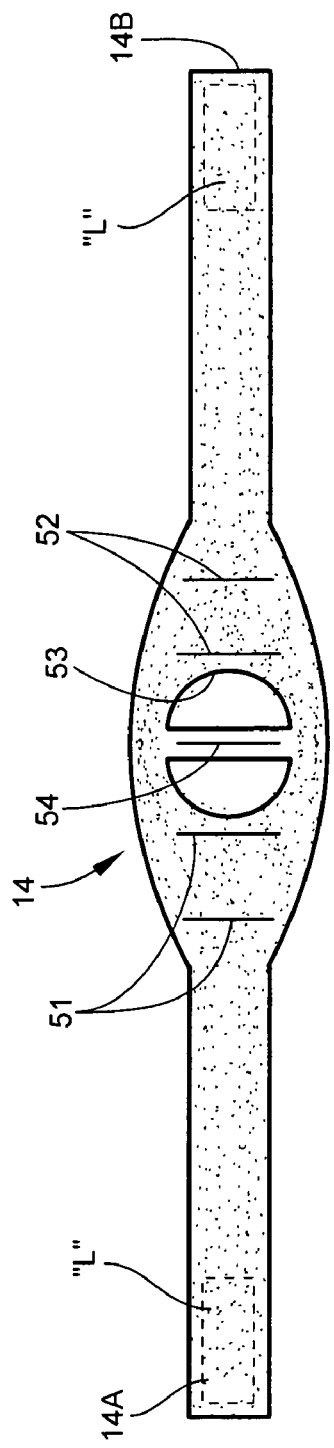
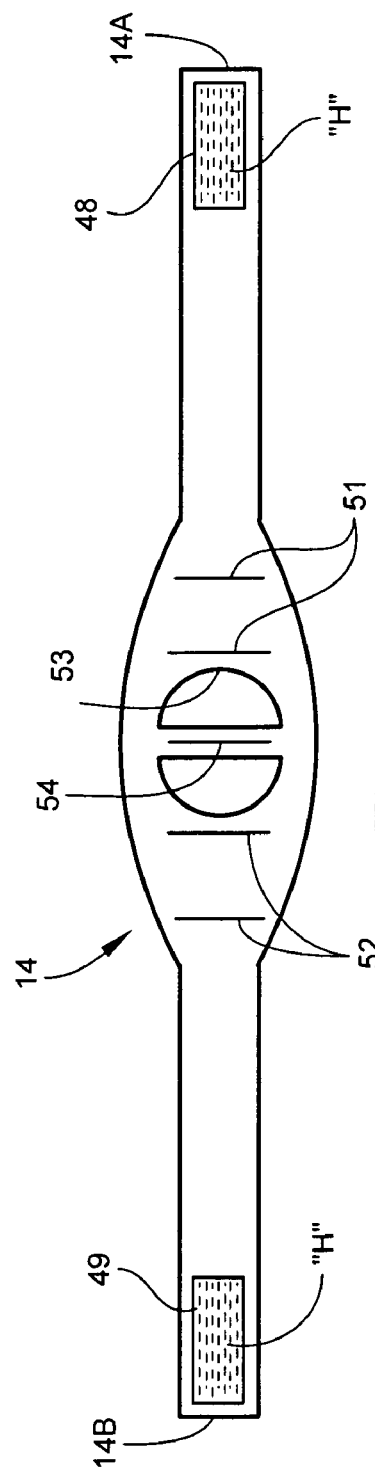
Fig. 15
Fig. 16

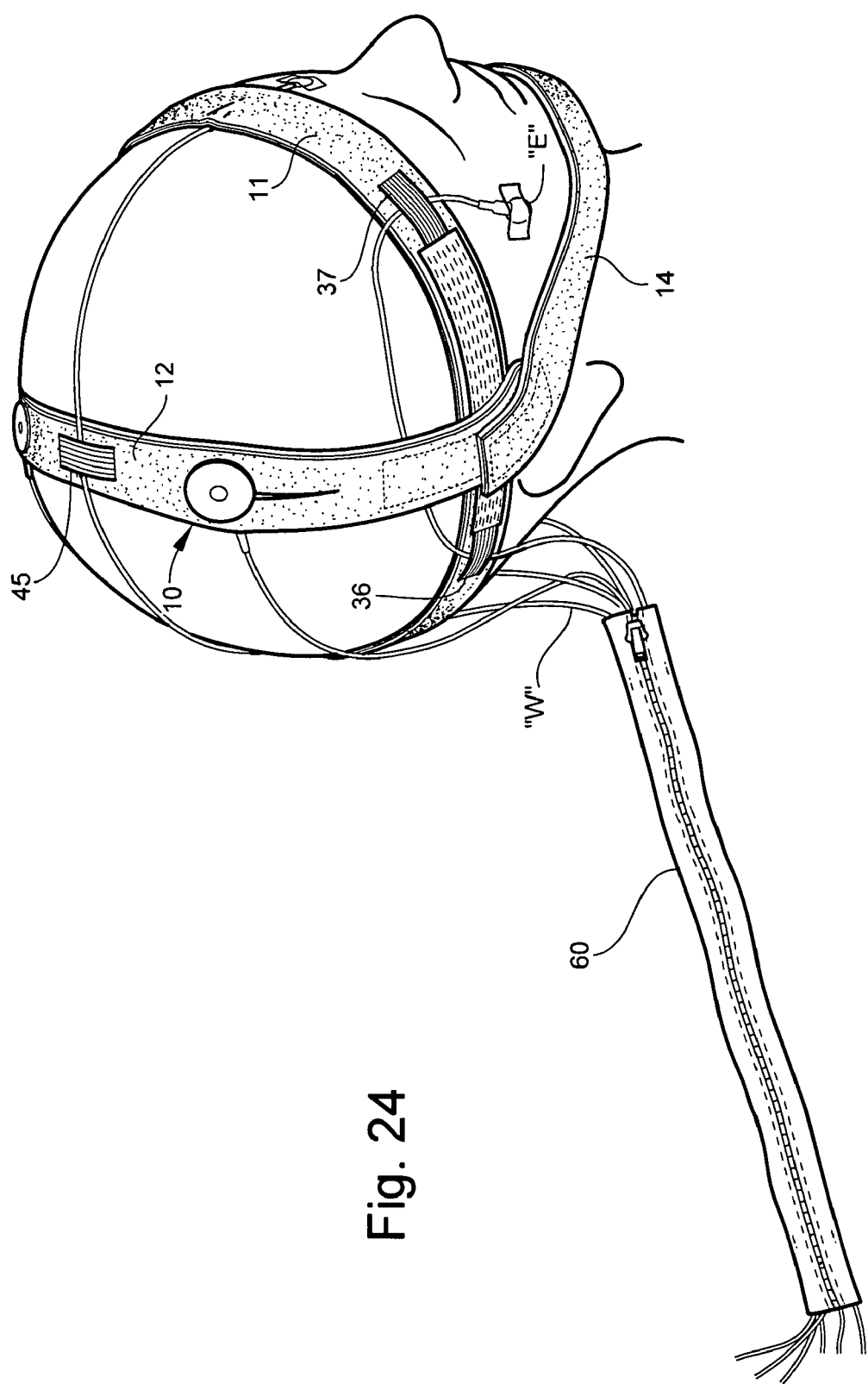

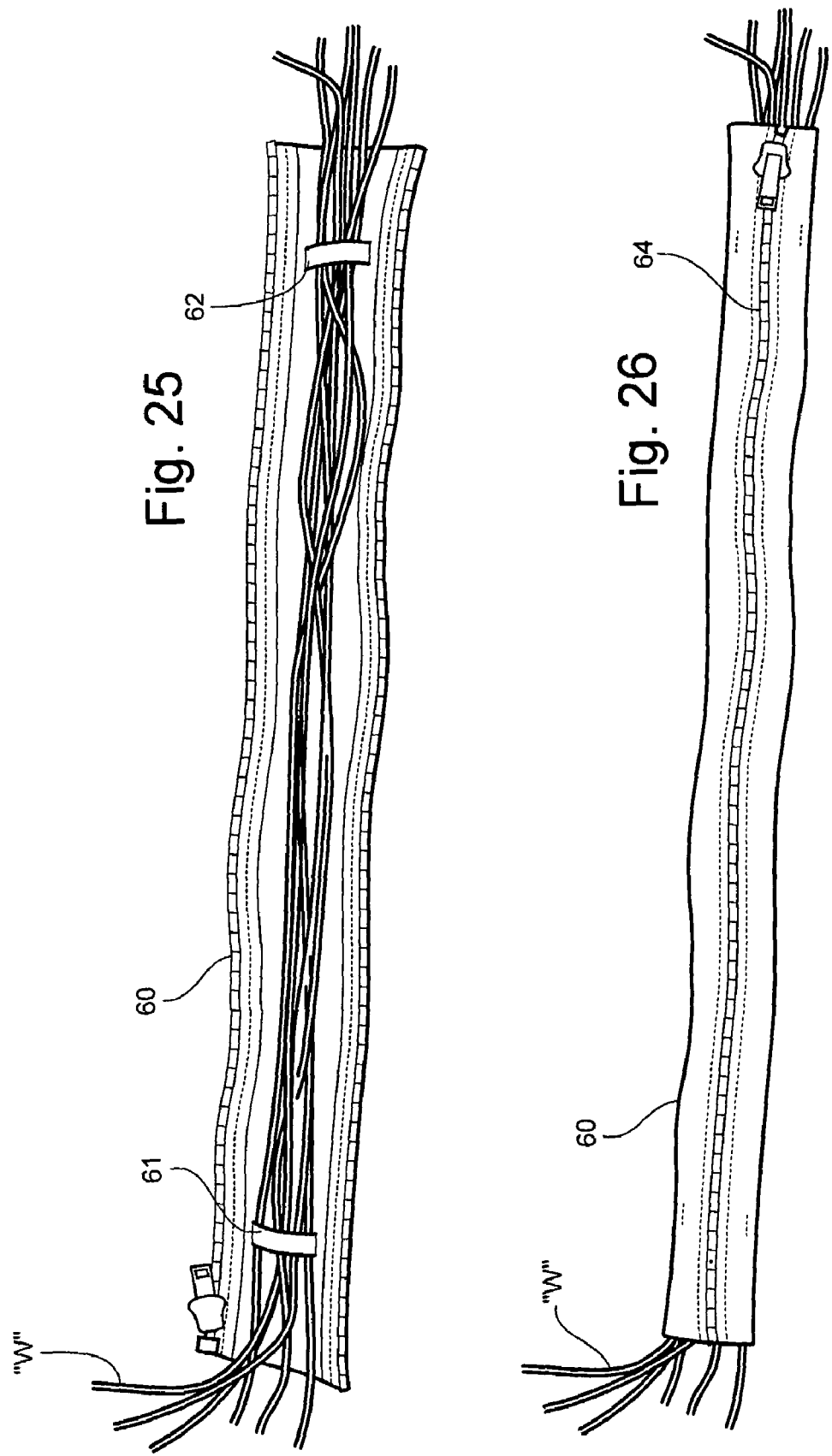

ELECTRODE HOLDER, HEADWEAR, AND WIRE JACKET ADAPTED FOR USE IN SLEEP APNEA TESTING

TECHNICAL FIELD AND BACKGROUND OF THE INVENTION

This invention relates generally to sleep apnea, and more specifically to an electrode holder, headwear, and wire jacket adapted for use in sleep apnea testing.

Sleep apnea is a serious, potentially life-threatening breathing disorder characterized by brief interruptions of breathing during sleep. In a given night, the number of involuntary breathing pauses or "apneic events" may be as high as 20 to 30 or more per hour. These breathing pauses are almost always accompanied by snoring between apnea episodes, although not everyone who snores has this condition. Sleep apnea can also be characterized by choking sensations. The frequent interruptions of deep, restorative sleep often lead to early morning headaches and excessive daytime sleepiness.

Certain mechanical and structural problems in the airway cause the interruptions in breathing during sleep. In some people, apnea occurs then the tongue and throat muscles relax during sleep and partially block the opening of the airway. When the muscles of the soft palate at the base of the tongue and the uvula relax and sag, the airway becomes blocked, making breathing labored and noisy and even stopping it altogether. Sleep apnea also can occur in obese people when an excess amount of tissue in the airway causes it to be narrowed. With a narrowed airway, the person continues their efforts to breathe, but air cannot easily flow into or out of the nose or mouth. Unknown to the person, this results in heavy snoring, periods of no breathing, and frequent arousals causing abrupt changes from deep sleep to light sleep.

During the apneic event, the person is unable to breathe in oxygen and to exhale carbon dioxide, resulting in low levels of oxygen and increased levels of carbon dioxide in the blood. The reduction in oxygen and increase in carbon dioxide alert the brain to resume breathing and cause an arousal. With each arousal, a signal is sent from the brain to the upper airway muscles to open the airway; breathing is resumed, often with a loud snort or gasp. Frequent arousals, although necessary for breathing to restart, prevent the patient from getting enough restorative, deep sleep.

The present invention relates to devices intended to promote the efficiency, quality and accuracy of sleep apnea testing. Testing is performed using a number of surface electrodes applied to the skin of a patient and connected through lead wires to a polysomnograph. The polysomnograph monitors the patient's sleep by converting electrical impulses in the body to a graphical representation. Quality and accuracy of any recording are directly related to the quality and accuracy of the input signals. Factors affecting input signals include improper placement of the electrodes and failure to properly secure the electrodes throughout testing.

Prior to testing, the patient is prepped or "hooked up" by a polysomnographic technologist. This involves attaching a number of electrodes on the patient's scalp, face, chin, chest, and legs. The process is painless, but generally time consuming. Each electrode is attached to the skin by completely filling a cavity of the electrode with an adhesive electrolyte gel, cream or paste. Standard commercial gels and pastes include ECG2 by Grass/AstroMed, Ten20 and Nu-Prep by Weaver, and Elefix by Nihon Kohden. In some cases, double sided adhesive washers are also used to hold the electrode in place. Failure to maintain a proper and firm attachment of the electrode to the skin throughout testing generally contributes to motion artifacts which disrupt the input signal and cause bad recordings. Overspreading of the electrolyte gel can also reduce the quality and accuracy of the recording. The electrolyte gel has a bad smell, and is generally cold and uncomfortable.

The present invention provides an alternative means for securing electrodes to the skin of the patient. The invention substantially reduces patient prep time, requires only a very small amount of gel, and provides improved electrode attachment resulting in reduced signal interruption and more accurate recordings.

SUMMARY OF INVENTION

Therefore, it is an object of the invention to provide medical devices which promote efficient, quality and accurate testing of sleep apnea patients.

It is another object of the invention to provide to maintain a stable and reliable input signal throughout sleep apnea testing.

It is another object of the invention to provide an improved means for attaching electrodes to the skin of the patient which requires the use of substantially less electrolyte gel—90% less in many cases.

It is another object of the invention to substantially reduce the messiness caused by the electrolyte gel when prepping the patient.

It is another object of the invention to substantially reduce the patient prep time.

It is another object of the invention to reduce movement artifact on the polysomnogram.

These and other objects of the present invention are achieved in the preferred embodiments disclosed below by providing an electrode holder adapted for cooperating with a strap applied to a body part of a patient to hold a surface electrode to the skin. The term "strap" is defined broadly herein to include any strap, band, cover, belt, patch or other article applied to a body part using any self-attachment means, such as mating ends of hook and loop fasteners, a releasable adhesive, snaps, buttons, and the like. The electrode holder includes a base and a post projecting from the base. The post is adapted for extending through the strap and into a cavity formed with the electrode. Means are provided for attaching the electrode holder to the strap. Once attached, the post secures the electrode in position thereby reducing motion artifacts caused by disturbance of the electrode after placement against the skin of the patient.

According to another preferred embodiment, the post includes a reinforcing member formed with the base.

Preferably, the reinforcing member has a generally x-shaped cross-section.

According to another preferred embodiment, the post further includes an electrode-penetrating tip extending from the reinforcing member.

Preferably, the electrode-penetrating tip has a rounded end to facilitate entry into the cavity of the electrode.

According to another preferred embodiment, the base comprises a thin flat disk.

According to another preferred embodiment, the means for attaching comprises hook fasteners located on the base and adapted for releasably mating with complementary loop fasteners located on the strap.

According to another preferred embodiment, the base and the post are integrally formed together of a molded polymer.

Preferably, the polymer is ABS plastic.

According to another preferred embodiment, the strap defines a post-receiving slit accommodating passage of the post through the strap and into the cavity of the electrode.

In another embodiment, the invention is a method for holding an electrode to the skin of a patient. The method includes the step of placing the electrode against the skin of the patient. An electrode holder is then attached to a strap. The electrode holder includes a post extending through the strap. The electrode is then covered with the strap, such that the post of the electrode holder inserts into a cavity formed with the electrode. The strap is then applied to a body part, whereby the post secures the electrode in position thereby reducing motion artifacts caused by disturbance of the electrode after placement against the skin of the patient.

BRIEF DESCRIPTION OF THE DRAWINGS

Some of the objects of the invention have been set forth above. Other objects and advantages of the invention will appear as the description proceeds when taken in conjunction with the following drawings, in which:

FIG. 15 is a view of the chin strap laid flat, and showing its outside major surface;

FIG. 16 is a view of the chin strap laid flat, and showing its inside major surface;

FIG. 24 is a further perspective view of a patient's head with the headwear and surface electrodes attached, and showing the lead wires bundled together in the wire jacket;

FIG. 25 is a view of the wire jacket laid open; and

FIG. 26 is a view of the wire jacket closed around the wires.

DESCRIPTION OF THE PREFERRED EMBODIMENT AND BEST MODE

Figure 1:
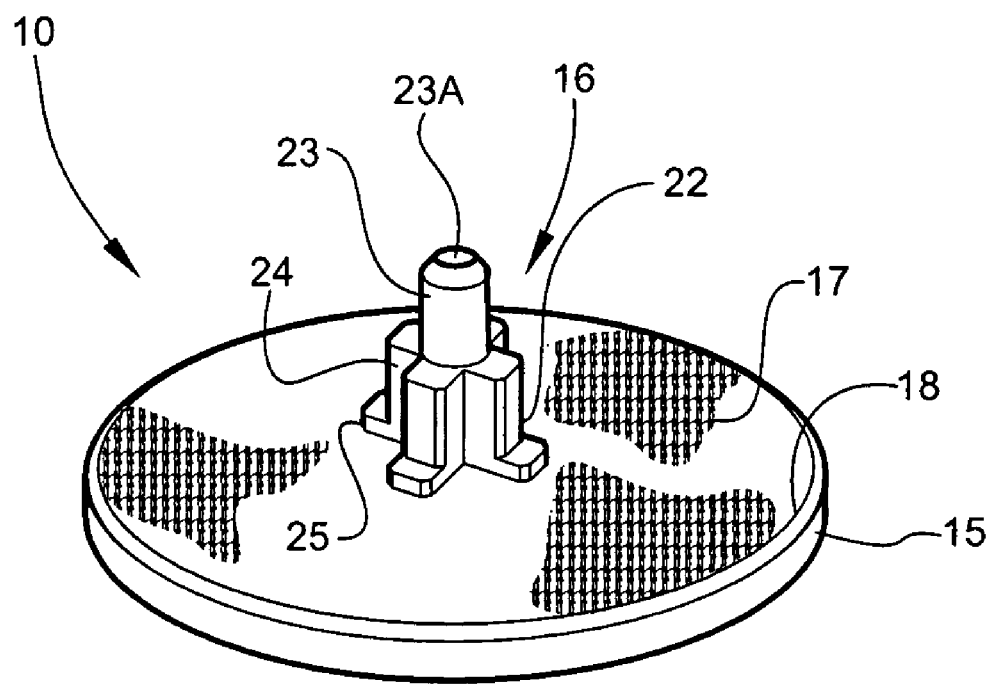
FIG. 1 is an isometric view of an electrode holder according to one preferred embodiment of the present invention.
Figure 2:
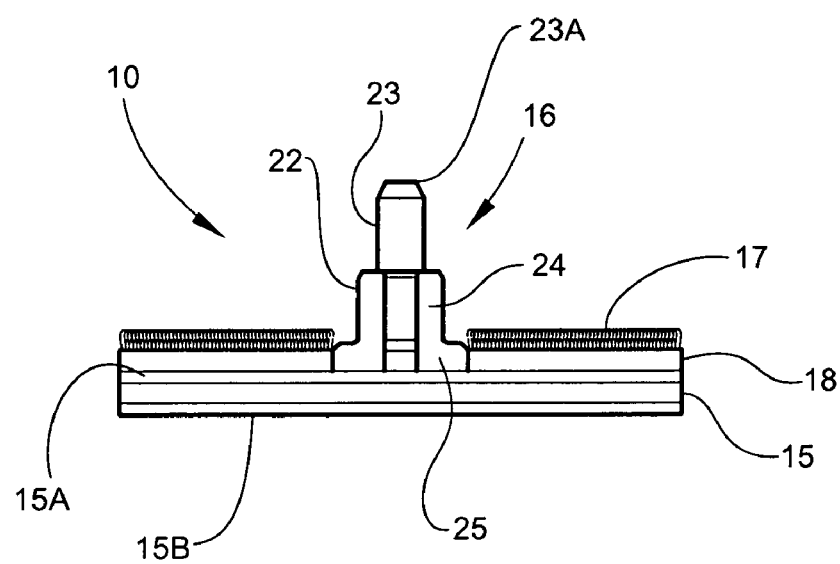
FIG. 2 is a side view of the electrode holder.
Figure 3:
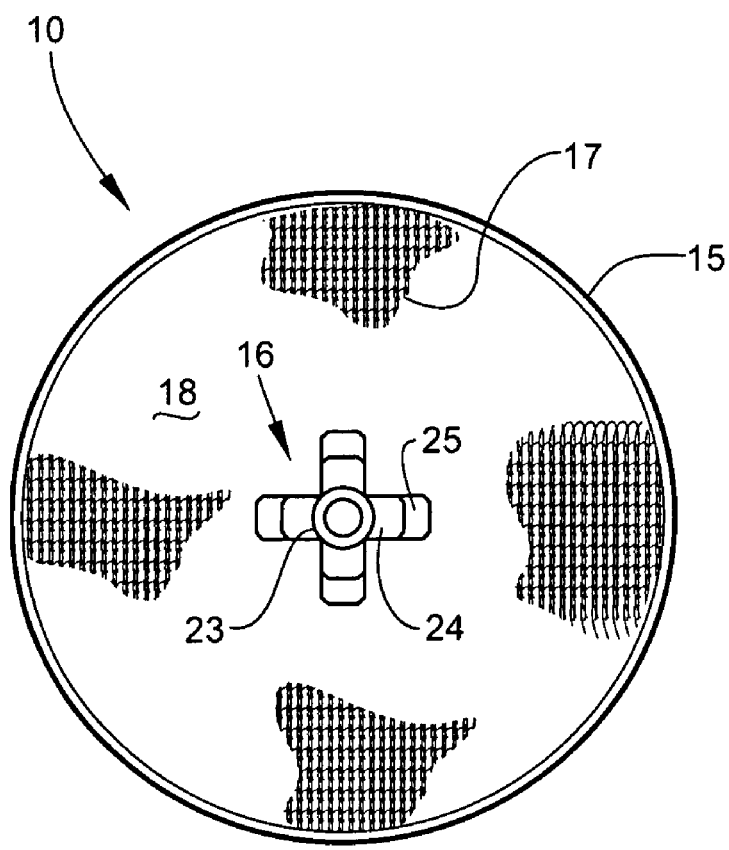
FIG. 3 is a top view of the electrode holder.
Figure 4:
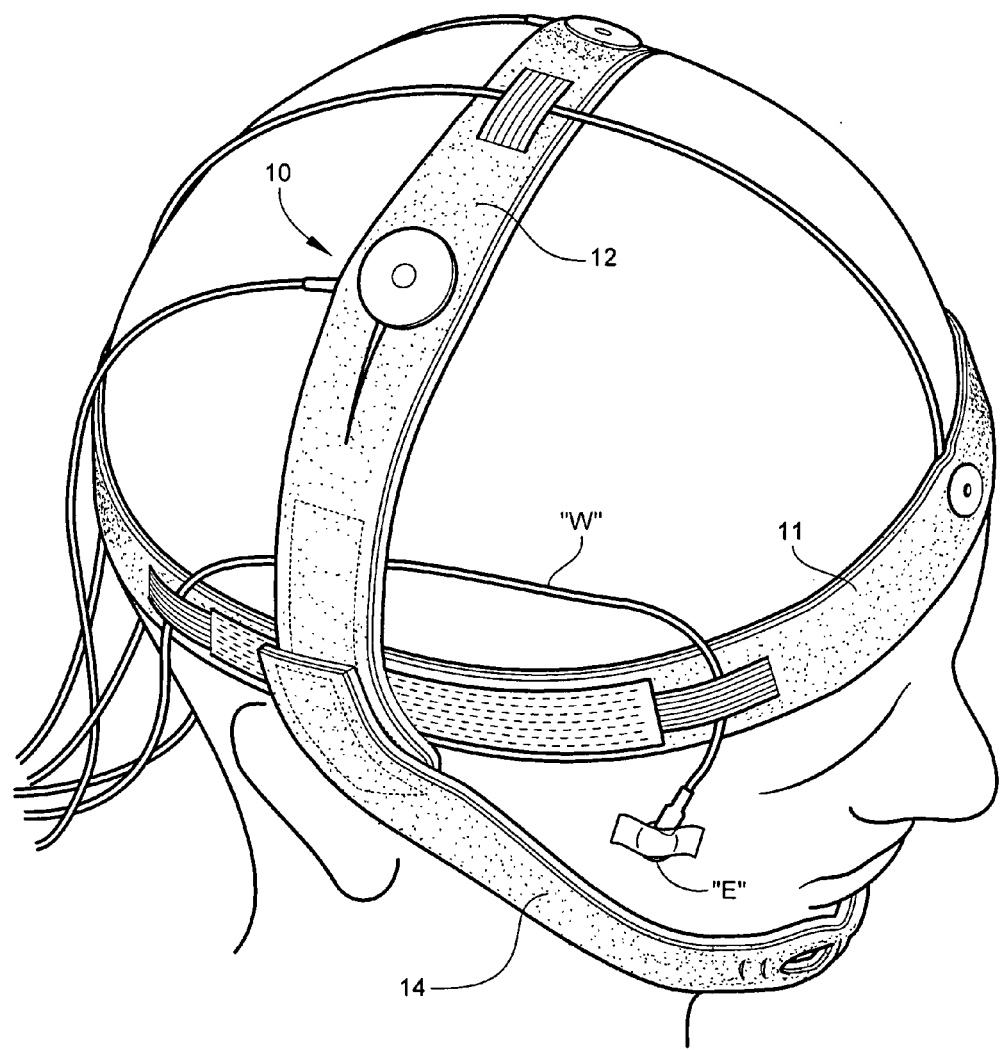
FIG. 4 is an isometric view of a patient's head with the electrodes and headwear attached.

Referring now specifically to the drawings, an electrode holder according to the present invention is illustrated in FIGS. 1–3, and shown generally at reference numeral 10. In sleep apnea testing, multiple electrode holders 10 are generally used on a single patient. The electrode holders 10 cooperate with various articles of headwear to hold respective surface electrodes to the skin of the patient. Preferably, the headwear comprises an assembly of fabric-covered neoprene head straps 11, 12, and 14 shown in FIG. 4 and described further below.

As previously discussed, sleep apnea is typically diagnosed in a polysomnography sleep test. An overnight polysomnography test involves monitoring brain waves, muscle tension, eye movement, respiration, oxygen level in the blood and audio monitoring for snoring, gasping, etc. A polysomnograph monitors the patient's sleep by converting electrical impulses in the body to a graphical representation. Many different activities are monitored by the polysomnograph during a sleep study. These include brain waves (EEG), eye movements (EOG), muscle activity (EMG), heartbeat (EKG), blood oxygen levels (SpO2) and respiration. Each of these activities is represented by graphical tracings on a polysomnogram.

Prior to testing, the patient is "hooked up" by a polysomnographic technologist. This involves locating the surface electrodes on the patient's scalp, face, chin, chest, and legs. The skin is first cleaned where the electrodes will be attached. Each electrode "E" has a round cup-shaped body (See FIGS. 6 and 7) which defines a small cavity "C" designed for receiving an adhesive material, such as an electrolyte gel, cream, or paste. The adhesive material serves to temporarily hold the electrode "E" to the skin during application of the headwear and throughout subsequent testing. Preferably, each electrode has a plastic-encased silver/silver chloride body with low DC offset potential, limited motion artifacts, and low frequency response. According to one embodiment, the electrode body is 12 mm in diameter and has a 2 mm cavity in the top for addition of the adhesive material. A flexible, small and durable gray lead wire "W" extends from the electrode "E" and terminates in a female safety connector (not shown). The lead wire "W" is generally available in 2, 3, 4, 5, 6, 8, & 10 foot load lengths.

After attaching the surface electrodes "E", the technician applies the head straps 11, 12, and 14 to the patient. The head straps 11, 12, 14 cooperate with the electrode holders 10 to firmly hold the electrodes "E" in place during testing. Since the quality and accuracy of any recording are directly related to the quality and accuracy of the input signals, it is important that the electrodes "E" are accurately placed and properly secured throughout the duration of the recording. Firm attachments minimize "popping" artifacts, which can easily be caused by patient movement during a sleep study.

Electrode Holder

Referring to FIGS. 1–3 and 5–7, each electrode holder 10 has a base 15 with opposing inside and outside major surfaces, 15A and 15B, respectively. An elongated post 16 projects from the inside surface 15A. The base 15 comprises a thin flat polymer disk, and hook fasteners 17 carried on a substrate 18 permanently adhered to the inside surface 15A. The outside surface 15B of the base 15 may include any desired indicia, such as a company logo or other source-indicating marking. The post 16 has an enlarged reinforcing member 22 integrally formed with the base 15, and an electrode-penetrating tip 23 designed for inserting into the cavity "C" of the electrode "E". Preferably, the reinforcing member 22 has a generally x-shaped cross-section and includes a plurality of circumferentially arranged columns 24 with respective feet 25 formed with the base 15. The base 15 and post 16 are preferably integrally formed together of a molded ABS plastic.

Figure 5:
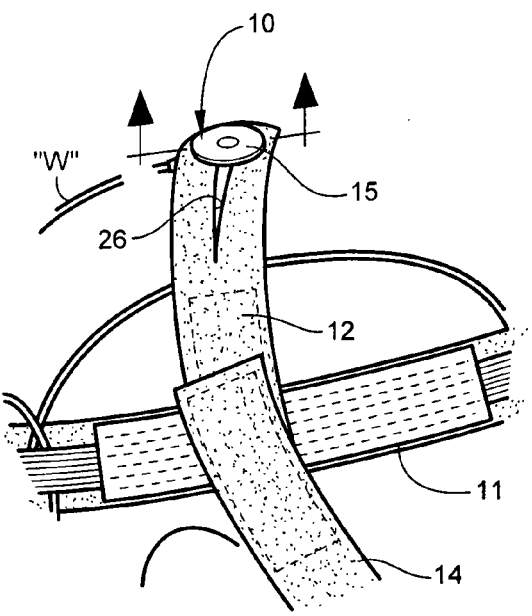
FIG. 5 is a fragmentary perspective view of the headwear with the electrode holder in place to hold the surface electrode to the skin.
Figure 6:
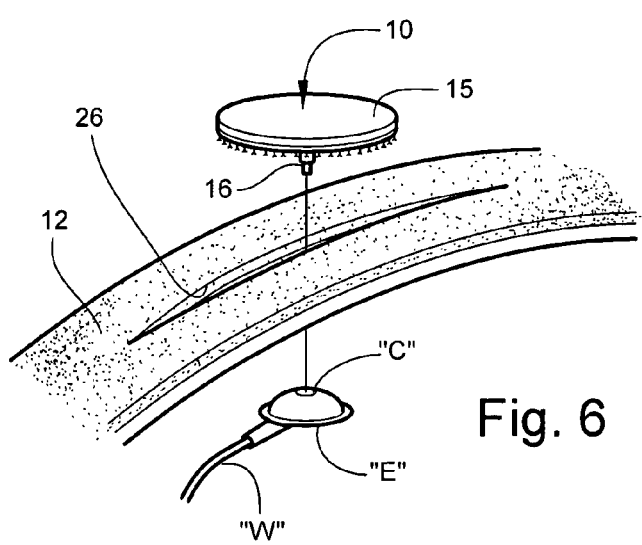
FIG. 6 is an exploded view showing the electrode holder removed from the cavity of the surface electrode.
Figure 7:
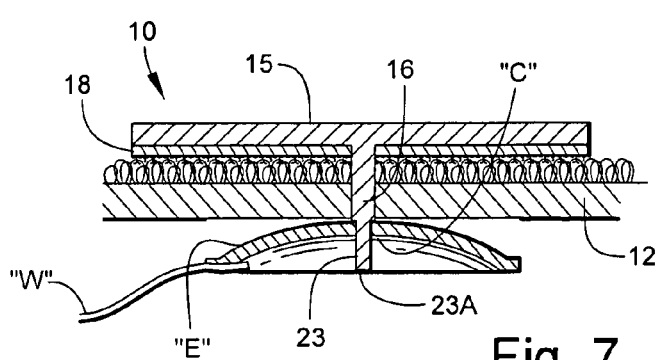
FIG. 7 is a cross-sectional view taken substantially along line 7—7 of FIG. 5.
Figure 8:
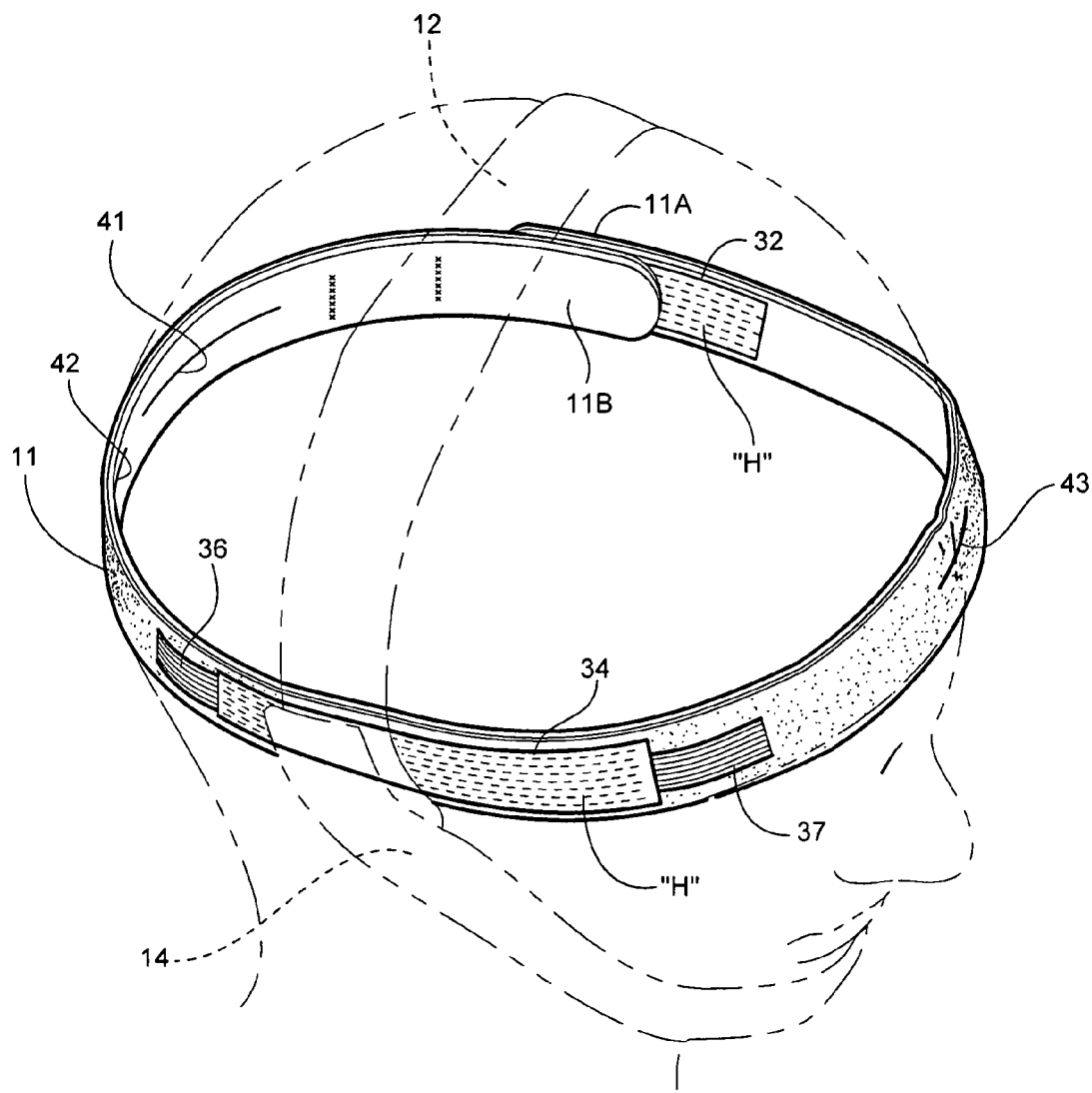
FIG. 8 is a perspective view of the head band with the top strap, chin strap and patient's head shown in phantom.
Figure 9:
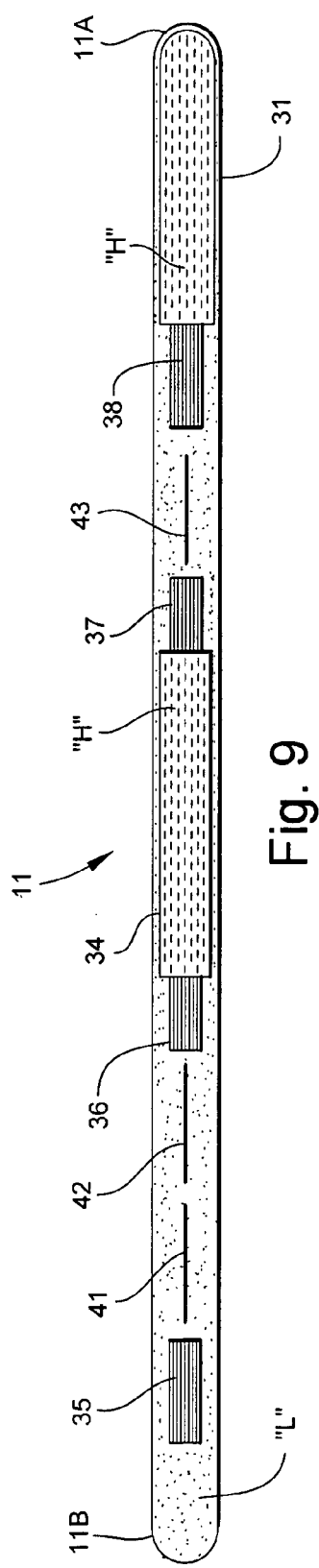
FIG. 9 is a view of the head band laid flat, and showing its outside major surface.
Figure 10:
FIG. 10 is a view of the head band laid flat, and showing its inside major surface.

As best shown in FIGS. 5–7, the electrode holder 10 is applied to the head strap 12 such that the post 16 extends through a longitudinal slit 26 formed with the strap 12. The electrode-penetrating tip 23 is then inserted into the gel-filled cavity "C" of the electrode "E". Preferably, the tip 23 has a rounded end 23A in order to facilitate its entry into the cavity "C". The hook fasteners 17 of the base 15 mate with the fabric cover (loops) 28 of the head strap 12, as shown in FIG. 7, to releasably secure the holder 10 to the strap 12, while the tip 23 of the post 16 firmly holds the electrode "E" in position against the skin of the patient.

Head Straps

Referring to FIGS. 8–16, the head straps 11, 12, 14 comprise a head band, a top strap, and a chin strap, respectively, which are interconnected and adapted for extending around and about the head of the patient. The head band 11, shown in FIGS. 8, 9, and 10, extends across the forehead, and has opposing ends 11A, 11B with complementary sections mating hook "H" and loop "L" fasteners which releasably and adjustably secure the band 11 to the patient. The end 11A has respective sections 31 and 32 of hook fasteners "H" on the outside and the inside of the band 11. The band 11 is applied to the head such that the loop fasteners (fabric) "L" on the outside of end 11B mate with the hook fasteners 32 on the inside of end 11A. This leaves the hook fastener section 31 on the outside of end 11A exposed. These fasteners 31 cooperate with a second hook fastener section 34 located on the outside of the band 11 to attach the top strap 12, as described below.

The outside of the band 11 further includes a number of spaced wire-management strips 35, 36, 37, and 38 for arranging and segregating lead wires "W" extending from the electrodes "E". The wire-management strips 35–38 are sewn to the band 11 at their respective opposite ends and include elastic yarns, such as spandex. By pulling the strip 35–38 slightly outwardly to create sufficient through-space, one or more lead wires "W" are fed through and held between a single strip 35–38 and the band 11. Longitudinal slits 41, 42, and 43 are also formed with the head band 11 for accommodating interconnection of the electrode holders 10 and surface electrodes "E", as previously described.

Figure 11:
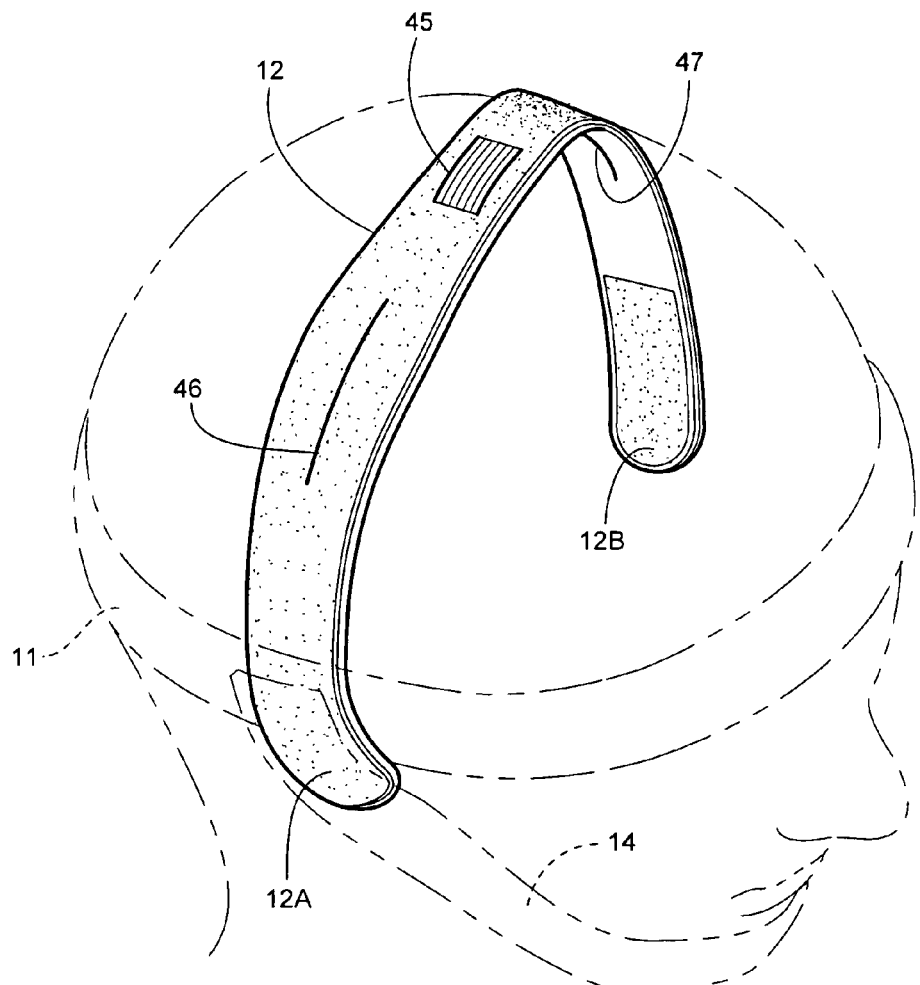
FIG. 11 is a perspective view of the top strap with the head band, chin strap, and patient's head shown in phantom.
Figure 12:
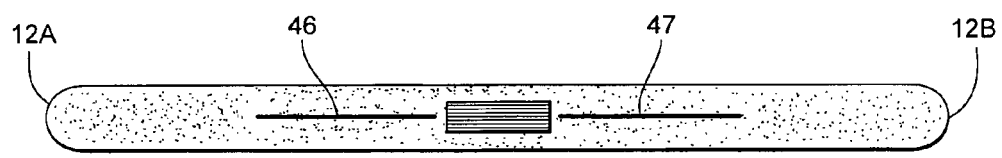
FIG. 12 is a view of the top strap laid flat, and showing its outside major surface.
Figure 13:
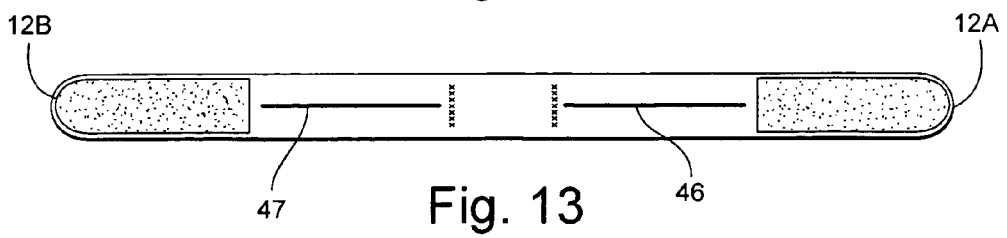
FIG. 13 is a view of the top strap laid flat, and showing its inside major surface.

FIGS. 11, 12, and 13 illustrate the top strap 12. The top strap 12 extends over the head of the patient, and has opposing ends 12A and 12B comprising both inside and outside loop fasteners (fabric) "F". The ends 12A, 12B mate with respective hook fastener sections 31, 34 of the head band 11 to releasably and adjustably secure the top strap 12 in position on the head. The top strap 12 has a center wire-management strip 45 located between a pair of longitudinal slits 46 and 47. The wire-management strip 45 serves to arrange and segregate electrode wires "W", while the slits 46, 47 accommodate interconnection of the electrode holders 10 and surface electrodes "E".

Figure 14:
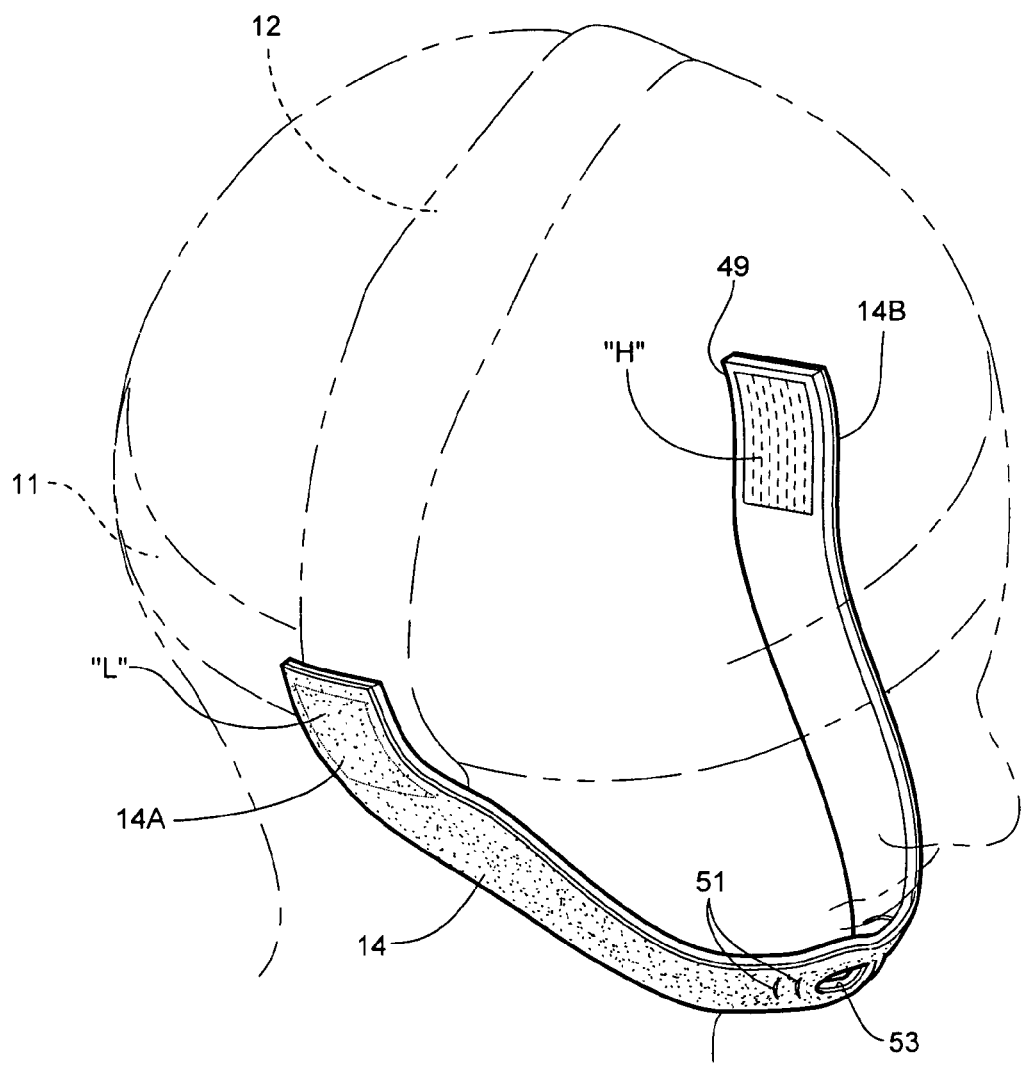
FIG. 14 is perspective view of the chin strap with the head band, top strap, and patient's head shown in phantom.
Figure 17:
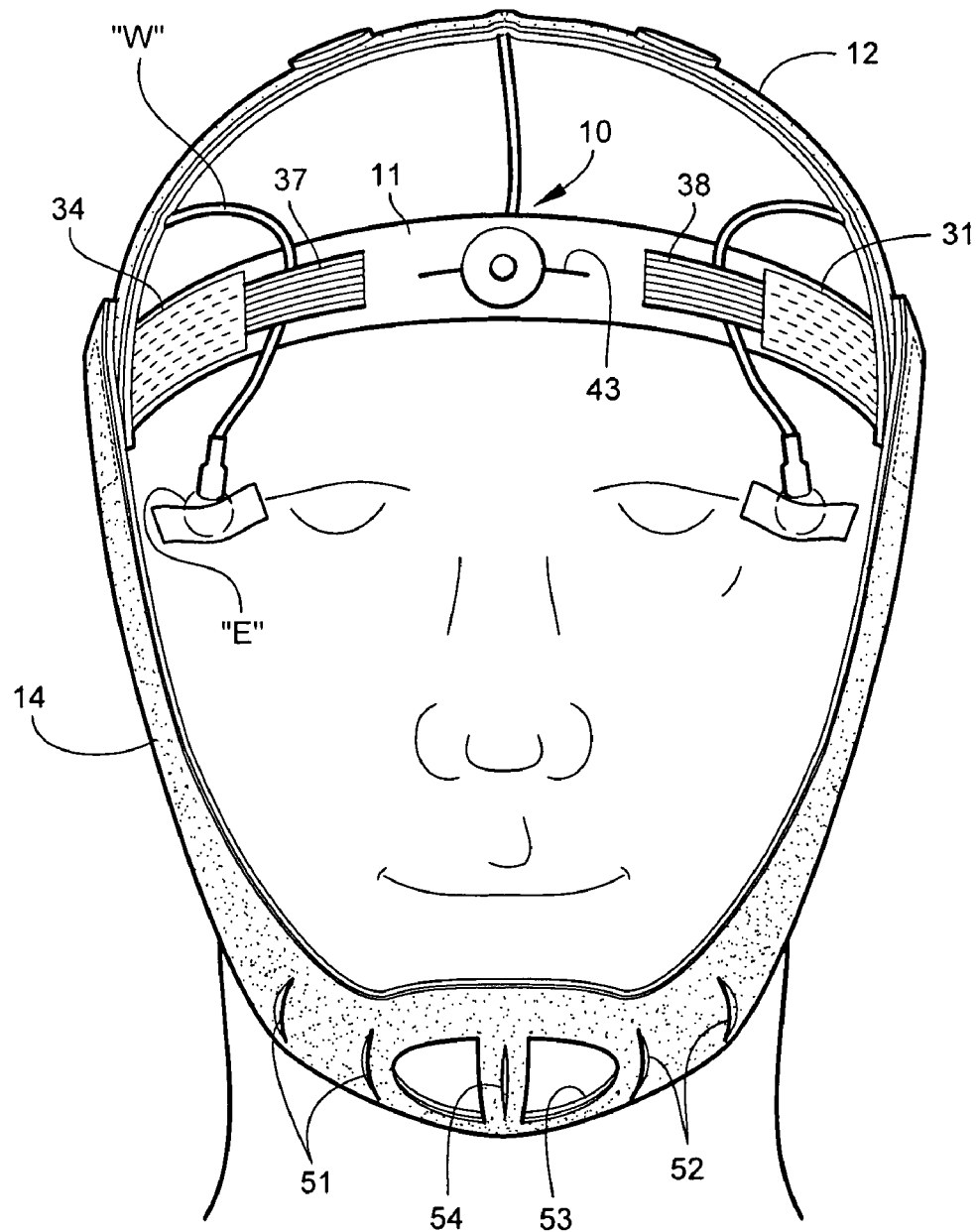
FIG. 17 is a front view of a patient's head with the headwear and surface electrodes attached.
Figure 18:
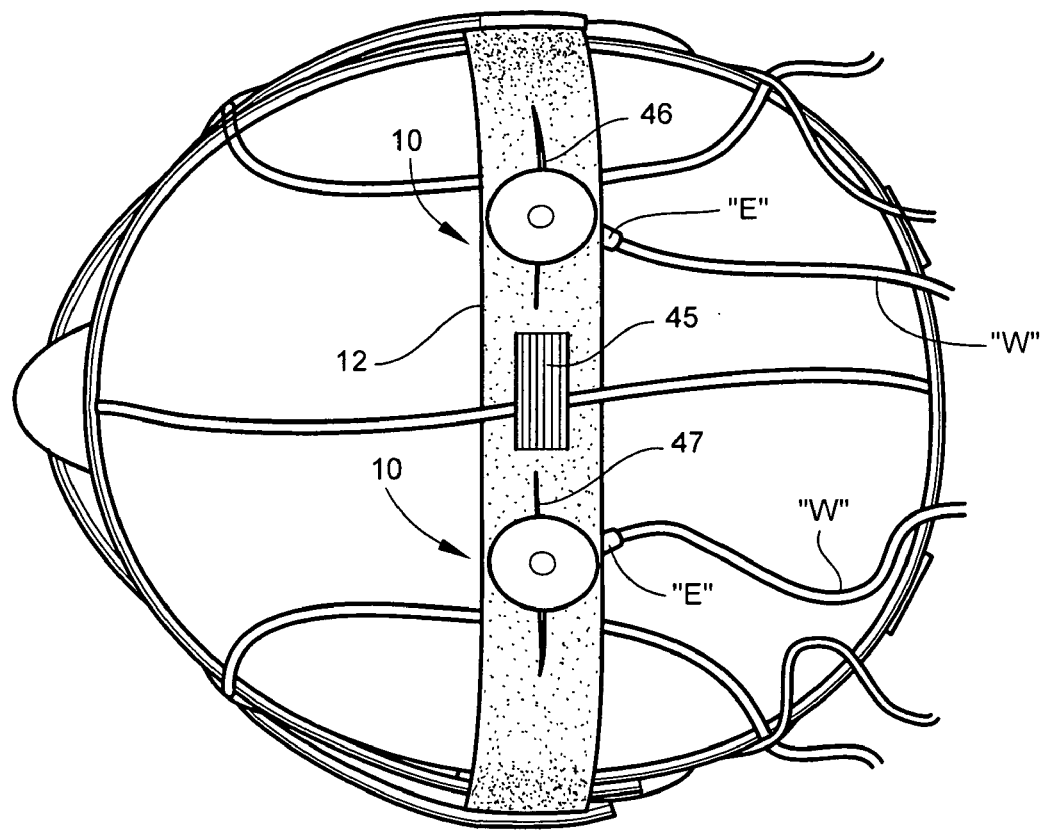
FIG. 18 is a top view of a patient's head with the headwear and surface electrodes attached.
Figure 19:
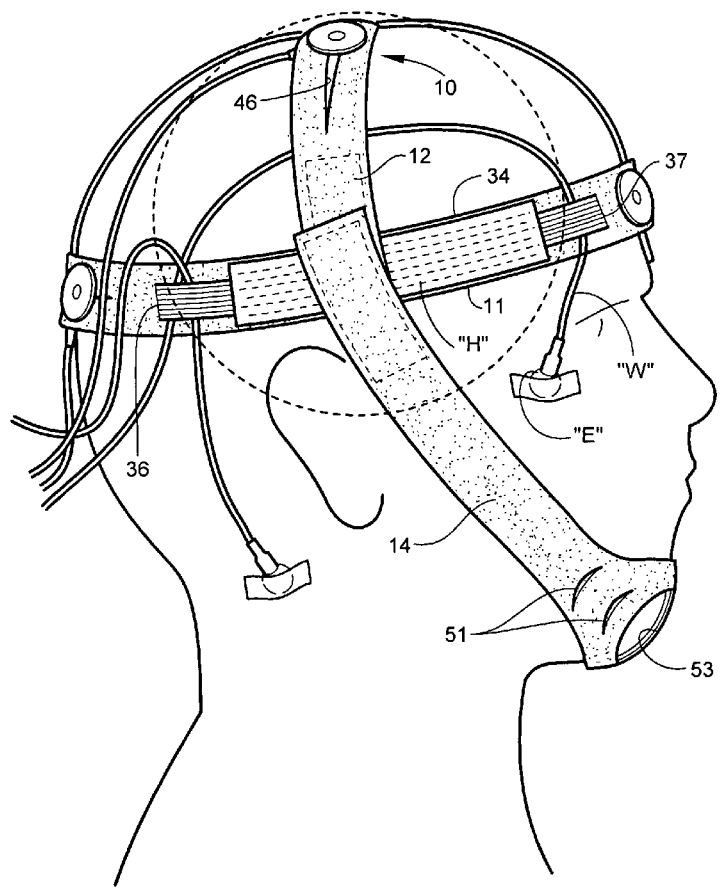
FIG. 19 is a right side view of a patient's head with the headwear and surface electrodes attached.
Figure 20:
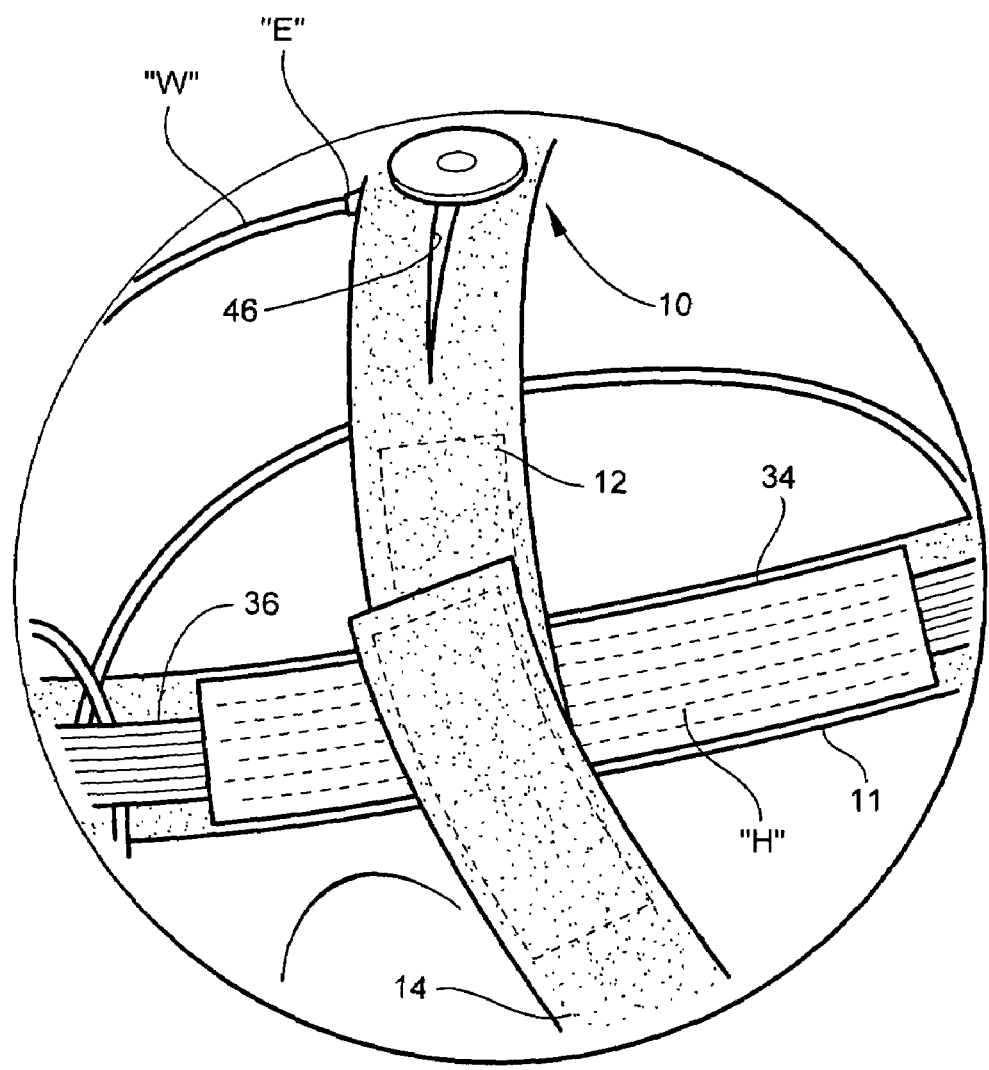
FIG. 20 is an enlarged view of the portion designated at reference numeral 20 in FIG. 19.
Figure 21:
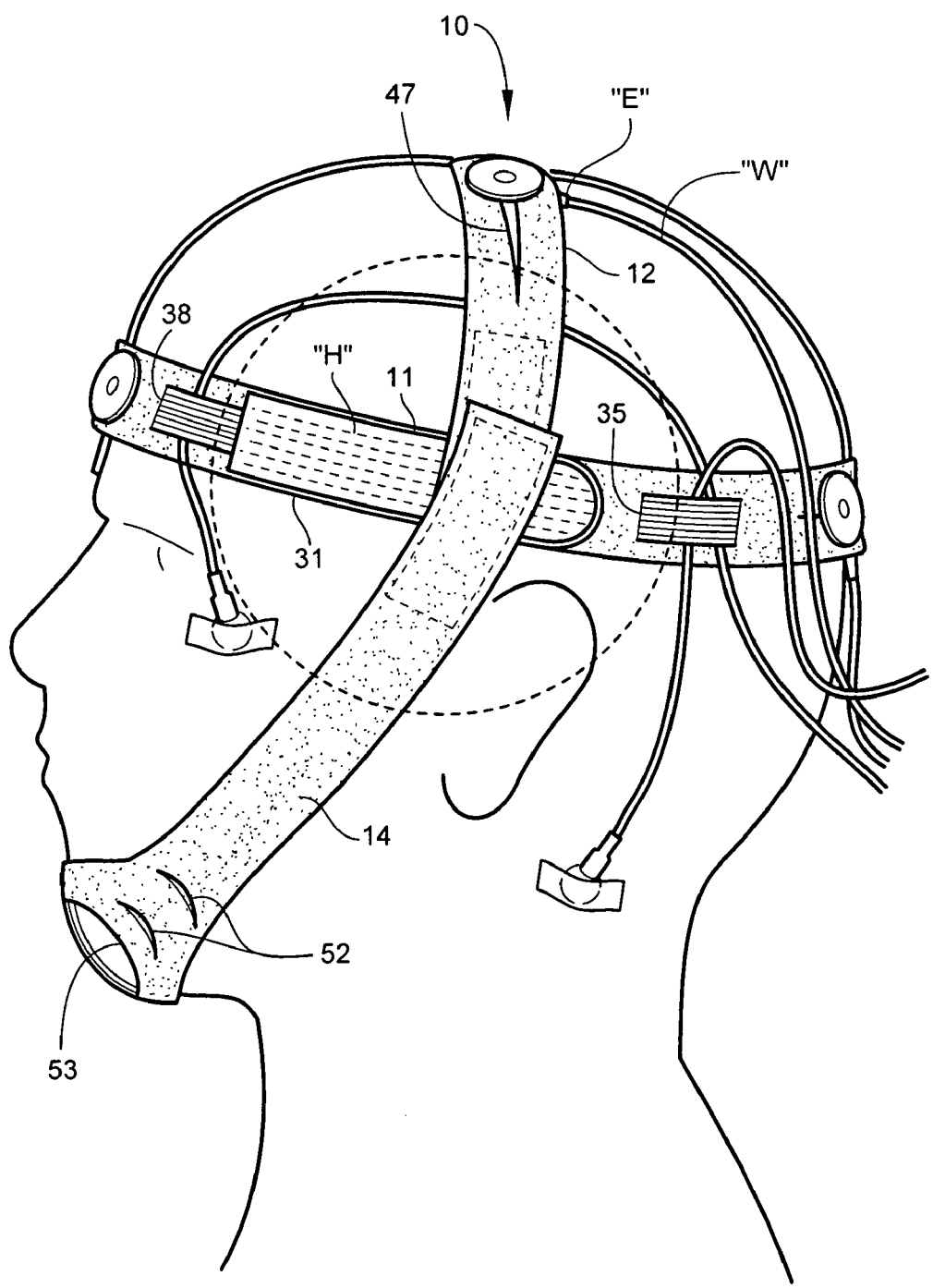
FIG. 21 is a left side view of a patient's head with the headwear and surface electrodes attached.
Figure 22:
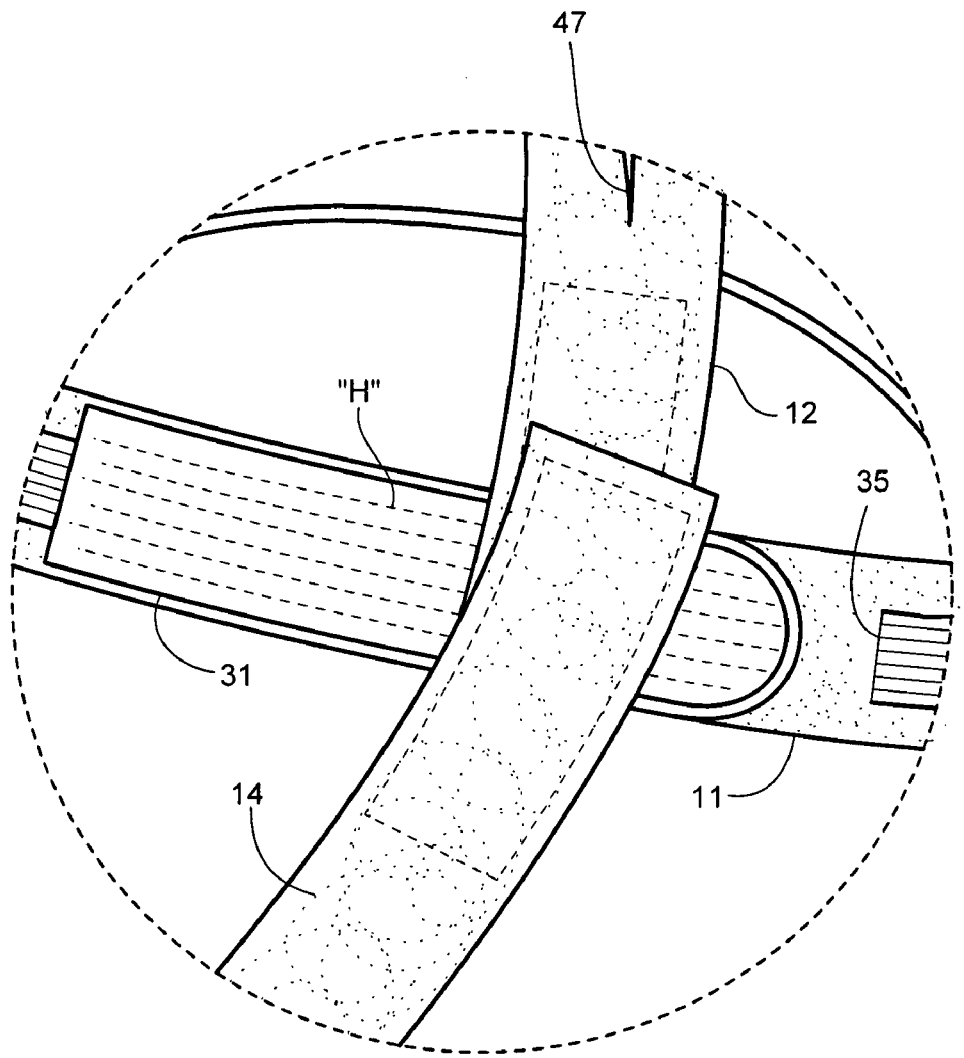
FIG. 22 is an enlarged view of the portion designated at reference numeral 22 in FIG. 21.

The chin strap 14 is best shown in FIGS. 14, 15, and 16. The chin strap 14 is designed to extend under the chin of the patient, and has sections 48 and 49 of hook fasteners "H" located on the inside of respective opposite ends 14A and 14B. These sections 48, 49 mate with the loop fasteners "L" located on the outside of the top strap 12 to releasably secure the chin strap 14 to the head. Pairs of lateral slits 51 and 52 are formed on opposite sides of a divided chin opening 53 with an additional slit 54 formed in the divider for accommodating interconnection of the electrode holders 10 and surface electrodes "E" attached to the chin. The chin strap 14 may also include one or more tube-retaining strips (not shown) designed for receiving and holding airway tubes used with a CPAP device.

FIGS. 17–22 illustrate complete assembly of the head band 11, top strap 12, and chin strap 14 with electrodes "E" attached to the head of the patient and wires "W" passing through respective wire-management strips 35–38 and 45. The hook "H" and loop "L" fasteners cooperate to provide a "touch" fastening system which securely holds the headwear in place, and offers ready and convenient size adjustment for increased effectiveness and added comfort. The neoprene rubber is soft, resilient, and breathable. The loop fasteners (fabric) "L" preferably comprise a cotton or cotton blend material.

Wire Jacket

Figure 23:
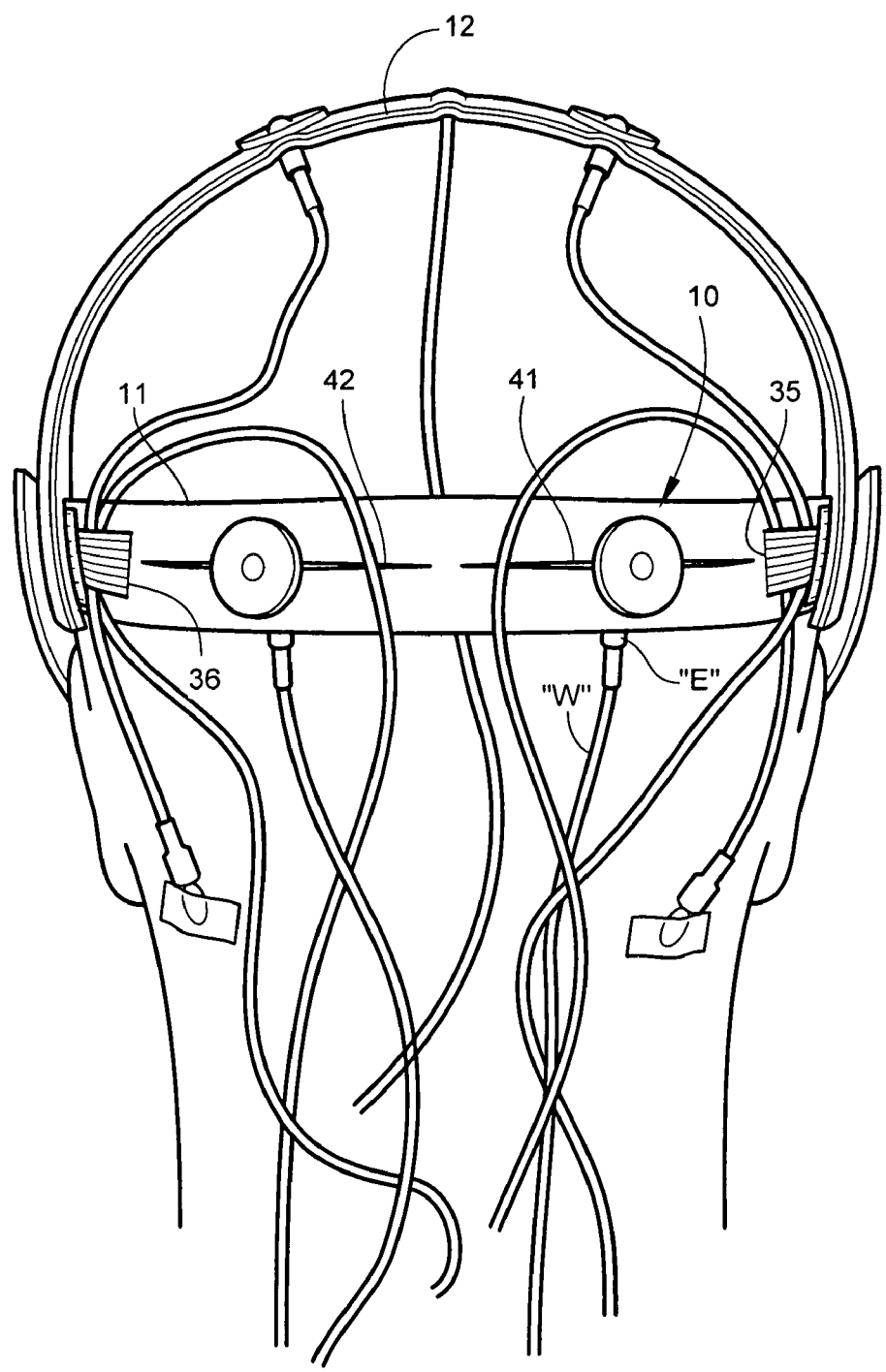
FIG. 23 is a back view of a patient's head with the headwear and surface electrodes attached.

Referring to FIGS. 24–26, the lead wires "W" extending from the surface electrodes "E" pass through the wire-management strips 35–38 and 45, as previously described, and are bundled together away from the patient within an elongated wire jacket 60. As shown in FIG. 25, interior loops 61 and 62 are sewn at their respective opposite ends to the jacket 60, and serve to further bundle and contain the wires "W" passing through the jacket 60. Preferably, the wire jacket 60 comprises a convenient longitudinal closure, such as a standard zipper 64, which closes the jacket 60 around the wires "W" as shown in FIGS. 23 and 26. By bundling the wires "W", the wire jacket 60 promotes reliable and uninterrupted signal input to the polysomnograph. In alterative embodiments, the jacket 60 may utilize other closure means including snap fasteners, buttons, hook and loop, and the like. The jacket 60 is between 18–30 inches long and is constructed of a fabric material, such as nylon.

An electrode holder, headwear, and wire jacket are described above. Various details of the invention may be changed without departing from its scope. Furthermore, the foregoing description of the preferred embodiment of the invention and best mode for practicing the invention are provided for the purpose of illustration only and not for the purpose of limitation—the invention being defined by the claims.

I claim:

1. An electrode holder adapted for cooperating with a strap applied to a body part of a patient to hold a surface electrode to the skin, said electrode holder comprising:
   (a) a base;
   (b) a post projecting from said base, and adapted for extending through the strap and into a cavity formed with the electrode, said post comprising a reinforcing member formed with said base and having a generally X-shaped cross-section; and (c) means for attaching said electrode holder to the strap, whereby said post secures said electrode in position thereby reducing motion artifacts caused by disturbance of said electrode after placement against the skin of the patient.

2. An electrode holder according to claim 1, wherein said post further comprises an electrode-penetrating tip extending from said reinforcing member.

3. An electrode holder according to claim 2, wherein said electrode-penetrating tip has a rounded end to facilitate entry into the cavity of the electrode.

4. An electrode holder according to claim 1, wherein said base comprises a thin flat disk.

5. An electrode holder according to claim 1, wherein said means for attaching comprises hook fasteners located on said base and adapted for releasably mating with complementary loop fasteners located on the strap.

6. An electrode holder according to claim 1, wherein said base and said post are integrally formed together of a molded polymer.

7. An electrode holder according to claim 6, wherein said polymer comprises ABS plastic.

8. In combination with a strap adapted for being applied to a body part of a patient, an electrode holder cooperating with said strap to hold a surface electrode to the skin, said electrode holder comprising:
(a) a base;
(b) a post projecting from said base, and extending through said strap for insertion into a cavity formed with the electrode; and
(c) hook fasteners located on said base and adapted for releasably mating with complementary loop fasteners located on the strap, whereby said post secures said electrode in position thereby reducing motion artifacts caused by disturbance of said electrode after placement against the skin of the patient.

9. A combination holder according to claim 8, wherein said post comprises a reinforcing member formed with said base.

10. A combination according to claim 9, wherein said reinforcing member has a generally x-shaped cross-section.

11. A combination according to claim 10, wherein said post further comprises an electrode-penetrating tip extending from said reinforcing member.

12. A combination according to claim 11, wherein said electrode-penetrating tip has a rounded end to facilitate entry into the cavity of the electrode.

13. A combination according to claim 8, wherein said base comprises a thin flat disk.

14. A combination according to claim 8, wherein said base and said post are integrally formed together of a molded polymer.

15. A combination according to claim 14, wherein said polymer comprises ABS plastic.

16. A combination according to claim 8, wherein said strap defines a post-receiving slit accommodating passage of said post through said strap and into the cavity of the electrode.

\* \* \* \* \*